(12) United States Patent
Zheng et al.

(10) Patent No.: US 12,226,612 B2
(45) Date of Patent: *Feb. 18, 2025

(54) COMPENSATION FOR MISSING READINGS FROM A GLUCOSE MONITOR IN AN AUTOMATED INSULIN DELIVERY SYSTEM

(71) Applicant: INSULET CORPORATION, Acton, MA (US)

(72) Inventors: Yibin Zheng, Hartland, WI (US); Joon Bok Lee, Acton, MA (US); Ashutosh Zade, San Diego, CA (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 399 days.

This patent is subject to a terminal disclaimer.

(21) Appl. No.: 17/715,589

(22) Filed: Apr. 7, 2022

(65) Prior Publication Data

US 2022/0226576 A1  Jul. 21, 2022

Related U.S. Application Data

(63) Continuation of application No. 16/791,648, filed on Feb. 14, 2020, now Pat. No. 11,324,889.

(51) Int. Cl.
*A61M 5/172* (2006.01)
*G06F 17/17* (2006.01)

(52) U.S. Cl.
CPC ........... *A61M 5/1723* (2013.01); *G06F 17/17* (2013.01); *A61M 2205/3303* (2013.01);
(Continued)

(58) Field of Classification Search
CPC . A61B 5/14532; A61B 5/4839; A61B 5/1495; A61B 5/7275; A61B 5/0002;
(Continued)

(56) References Cited

U.S. PATENT DOCUMENTS

| 5,007,286 A | 4/1991 | Malcolm et al. |
| 6,553,841 B1 | 4/2003 | Blouch |

(Continued)

FOREIGN PATENT DOCUMENTS

| AU | 2015200834 A1 | 3/2015 |
| EP | 2897071 B1 | 5/2019 |

(Continued)

OTHER PUBLICATIONS

International Search Report and Written Opinion for the International Patent Application No. PCT/US2022/013470, mailed May 6, 2022, 14 pages.

(Continued)

*Primary Examiner* — Manuel A Mendez
(74) *Attorney, Agent, or Firm* — GOODWIN PROCTER LLP

(57) ABSTRACT

Exemplary embodiments may address the problem of missing blood glucose concentration readings from a glucose monitor that transmits blood glucose concentration readings over a wireless connection due to problems with the wireless connection. In the exemplary embodiments, an automated insulin delivery (AID) device uses an estimate in place of a missing blood glucose concentration reading in determining a predicted future blood glucose concentration reading for a user. Thus, the AID device is able to operate normally in generating insulin delivery settings despite not receiving a current blood glucose concentration reading for a current cycle. There is no need to suspend delivery of insulin to the user due to the missing blood glucose concentration reading.

20 Claims, 11 Drawing Sheets

(52) U.S. Cl.
CPC .............. *A61M 2205/3331* (2013.01); *A61M 2205/3507* (2013.01); *A61M 2205/3553* (2013.01); *A61M 2205/52* (2013.01); *A61M 2230/201* (2013.01)

(58) Field of Classification Search
CPC ............ A61M 5/1723; A61M 5/14244; A61M 5/142; G16H 20/17; G16H 50/50; G16H 40/63; G16H 50/20; G16H 20/10
See application file for complete search history.

(56) References Cited

U.S. PATENT DOCUMENTS

| | | | |
|---|---|---|---|
| 9,233,204 | B2 | 1/2016 | Booth et al. |
| 10,583,250 | B2 | 3/2020 | Mazlish et al. |
| 10,737,024 | B2 | 8/2020 | Schmid |
| 10,987,468 | B2 | 4/2021 | Mazlish et al. |
| 11,197,964 | B2 | 12/2021 | Sjolund et al. |
| 11,260,169 | B2 | 3/2022 | Estes |
| 11,324,889 | B2 * | 5/2022 | Zheng .................... G16H 40/67 |
| 2008/0172026 | A1 | 7/2008 | Blomquist |
| 2009/0054753 | A1 | 2/2009 | Robinson et al. |
| 2011/0124996 | A1 | 5/2011 | Reinke et al. |
| 2014/0146202 | A1 | 5/2014 | Boss et al. |
| 2015/0120317 | A1 | 4/2015 | Mayou et al. |
| 2015/0134265 | A1 | 5/2015 | Kohlbrecher et al. |
| 2015/0359490 | A1 | 12/2015 | Massey et al. |
| 2015/0366945 | A1 | 12/2015 | Greene |
| 2016/0038673 | A1 | 2/2016 | Morales |
| 2016/0354543 | A1 | 12/2016 | Cinar et al. |
| 2017/0049386 | A1 | 2/2017 | Abraham et al. |
| 2017/0348482 | A1 | 12/2017 | Duke et al. |
| 2018/0169334 | A1 | 6/2018 | Grosman et al. |
| 2018/0200434 | A1 | 7/2018 | Mazlish et al. |
| 2018/0200438 | A1 | 7/2018 | Mazlish et al. |
| 2018/0289891 | A1 | 10/2018 | Finan et al. |
| 2019/0076600 | A1 | 3/2019 | Grosman et al. |
| 2020/0046268 | A1 | 2/2020 | Patek et al. |
| 2020/0342974 | A1 | 10/2020 | Chen et al. |
| 2021/0098105 | A1 | 4/2021 | Lee et al. |
| 2022/0023536 | A1 | 1/2022 | Graham et al. |

FOREIGN PATENT DOCUMENTS

| | | |
|---|---|---|
| JP | 2002085556 A | 3/2002 |
| JP | 2019525276 A | 9/2019 |
| WO | 2005082436 A1 | 9/2005 |
| WO | 2007078937 A1 | 7/2007 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2013177565 A1 | 11/2013 |
| WO | 2014123998 A2 | 8/2014 |
| WO | 2015187366 A1 | 12/2015 |
| WO | 2016004088 A1 | 1/2016 |
| WO | 2017091624 A1 | 6/2017 |
| WO | 2018067748 A1 | 4/2018 |
| WO | 2018136799 A1 | 7/2018 |
| WO | 2019213493 A1 | 11/2019 |
| WO | 2019246381 A1 | 12/2019 |
| WO | 2021011738 A1 | 1/2021 |

OTHER PUBLICATIONS

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

International Search Report and Written Opinion for the International Patent Application No. PCT/US22/019080, mailed Jun. 7, 2022, 14 pages.

International Search Report and Written Opinion for the International Patent Application No. PCT/US22/019664, mailed Jun. 7, 2022, 14 pages.

International Search Report and Written Opinion for the International Patent Application No. PCT/US21/060618, mailed Mar. 21, 2022, 15 pages.

Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial beriod in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Fox, Ian G .; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2022/012896, mailed Apr. 22, 2022, 15 pages.

* cited by examiner

COMPENSATION FOR MISSING READINGS FROM A GLUCOSE MONITOR IN AN AUTOMATED INSULIN DELIVERY SYSTEM

RELATED APPLICATIONS

This application is a continuation of U.S. patent application Ser. No. 16/791,648, filed Feb. 14, 2020, the contents of which are incorporated herein by reference in their entirety.

BACKGROUND

Automated Insulin Delivery (AID) systems typically rely on blood glucose concentration readings from a glucose monitor on an on-going basis to adjust how much insulin to deliver to a user. In some AID systems, there is a feedback loop where the blood glucose concentration readings are fed back to an insulin delivery device to adjust the next insulin delivery so that the blood glucose concentration of the user moves toward a target. Proper operation of such AID systems may require that an updated blood glucose concentration reading be received each control cycle.

In some AID systems, the blood glucose concentration readings are received wirelessly from a glucose monitor. This is more convenient for the user than a wired connection in that there is no need for potentially annoying wiring to run between the insulin delivery device and the glucose monitor. Such wireless connections between the insulin delivery device and the glucose monitor may be unreliable. In particular, the wireless connections may be dropped for intervals or may become otherwise temporarily inoperable. During such interruptions, an updated blood glucose concentration reading is not received by the insulin delivery device. Hence, conventionally, the response is to freeze the system so that no insulin is delivered to the user during the interruption. The interruption may be extended in conventional AID systems because the system relies on multiple recent blood glucose concentration values to determine insulin delivery settings. Thus, multiple updated blood glucose concentration readings must be received over multiple control cycles before the AID system resumes normal operation.

SUMMARY

In accordance with an exemplary embodiment, an AID device includes a wireless interface with a glucose sensor for providing blood glucose concentration readings of a user. The AID device also includes an insulin reservoir for holding insulin to deliver to the user and a storage media for storing programming instructions, the blood glucose concentration readings received from the glucose sensor, predicted future blood glucose concentration readings for the user and insulin delivery history for the user. The device additionally includes a processor for executing the programming instructions in the storage media. Where a current blood glucose concentration reading for the user is successfully received over the wireless interface from the glucose sensor for a current control cycle, the instructions cause the processor to set insulin delivery settings for delivery of the insulin to the user from the insulin reservoir for the current control cycle based on the predicted future blood glucose concentration readings for the user. The predicted future blood glucose concentration readings are based on the blood glucose concentration readings from the glucose sensor from previous control cycles and insulin action of previously delivered insulin. Where the current blood glucose concentration reading for the user is not successfully received over the wireless interface from the glucose sensor for the current control cycle, the instructions cause the processor to estimate the at least one blood glucose concentration reading that was not successfully received over the wireless interface from the glucose sensor. The instructions also cause the processor to set the insulin delivery settings for delivery of the insulin to the user from the insulin reservoir for the current control cycle based on the predicted future blood glucose concentrations for the user. The predicted future blood glucose concentrations are based on the blood glucose concentration readings from the glucose sensor from previous control cycles, insulin action of previously delivered insulin and an estimate of the current blood glucose concentration reading that was not successfully received over the wireless interface from the glucose sensor.

The estimate of the current blood glucose concentration reading may be one of the predicted future blood glucose concentrations for the current control cycle. The estimate of the current blood glucose concentration reading instead may be determined by applying interpolation of past blood glucose concentration readings. The estimate of the of the current blood glucose concentration reading may be determined by summing a most recent received blood glucose concentration reading with an average change between most recent ones of the blood glucose concentration readings. Alternatively, the estimate of the current blood glucose concentration reading may be a most recent received blood glucose concentration reading.

In accordance with an exemplary embodiment, a method is performed by a processor. Per this method, where a current blood glucose concentration reading for a user is successfully received by an automated insulin delivery (AID) device over a wireless interface from the glucose sensor for a current control cycle, insulin delivery settings for delivery of the insulin by the AID device to the user from an insulin reservoir of the AID device are set for the current control cycle based on predicted future blood glucose concentrations for the user. The predicted future blood glucose concentrations are based on blood glucose concentration readings from the glucose sensor for previous control cycles and insulin action of previously delivered insulin. Where the blood glucose concentration reading for the user is not successfully received by the AID device over the wireless interface from the glucose sensor for the current control cycle, the current blood glucose concentration reading that was not successfully received over the wireless interface from the glucose sensor is estimated, and the insulin delivery settings for delivery of the insulin to the user from the insulin reservoir for the current control cycle are set based on the predicted future blood glucose concentrations for the user. The predicted future blood glucose concentrations are based on the blood glucose concentration readings from the glucose sensor from previous control cycles, insulin action of previously delivered insulin and an estimate of the current blood glucose concentration reading that was not successfully received over the wireless interface from the glucose sensor. Instructions for performing the method may be stored on a non-transitory computer-readable storage medium.

In accordance with an exemplary embodiment, a method is performed by an automated insulin delivery (AID) device. Per this method, blood glucose concentration readings for a user are received from a glucose sensor over a wireless interface at the AID device for control cycles. During normal operation, a blood glucose concentration reading is received for each of the control cycles. The received blood glucose concentration readings received from the glucose sensor are stored in storage accessible by the AID device. Where, for a given control cycle, a blood glucose concentration reading for the user is not received at the AID device from the glucose sensor over the wireless interface, an estimate of the blood glucose concentration reading for the user for the given control cycle is determined. The stored blood glucose concentration readings and the determined estimate for the given control cycle are used to predict a future blood glucose concentration reading. Insulin delivery settings of the AID device are set based on the predicted future blood glucose concentration for the user. When communication over the wireless interface with the glucose sensor is reestablished, the estimate of the blood glucose concentration reading for the user for the given control cycle is replaced with a blood glucose concentration reading for the user from the glucose monitor for the given cycle in determining an estimate of the blood glucose concentration reading for the user for a next control cycle. Instructions for performing the method may be stored on a non-transitory computer-readable storage medium The determining an estimate of the blood glucose concentration reading for the user for the given control cycle may include determining a trend of blood glucose concentration values from the received blood glucose concentration readings and using the trend to determine the estimate. The using the trend of blood glucose concentration values may include performing extrapolation based on the trend to obtain the estimate or performing interpolation based on the trend to obtain the estimate. The method may include the additional operation of using the using the blood glucose concentration reading for the given cycle in setting the insulin delivery settings of the AID device.

DETAILED DESCRIPTION

Exemplary embodiments address the problem of missing blood glucose concentration readings from a glucose monitor that transmits blood glucose concentration readings over a wireless connection due to problems with the wireless connection. In the exemplary embodiments, an AID device uses an estimate in place of a missing blood glucose concentration reading in determining a predicted future blood glucose concentration reading for a user. Thus, the AID device is able to operate normally in generating insulin delivery settings despite not receiving a current blood glucose concentration reading for a current cycle. There is no need to suspend delivery of insulin to the user due to the missing blood glucose concentration reading.

The estimate of the missing blood glucose concentration reading may be determined in a number of different ways. First, the estimate may be a past determined prediction of the blood glucose concentration reading for the current control cycle. Second, the estimate may be an interpolated value. Third, the estimate may be the most recently received blood glucose concentration reading. Other ways of calculating the estimate may also be used.

The AID device keeps and uses a history of the blood glucose concentration readings. When one or more blood glucose concentration readings from the glucose monitor have not been received and the wireless connectivity with the AID device is restored, missing blood glucose concentration readings may be sent from the glucose monitor to the AID device and used to backfill the missing blood glucose concentration readings. Alternatively, in some exemplary embodiments, the missing blood glucose concentration readings may be backfilled with predicted blood glucose concentration readings for the associated control cycles.

Figure 1:
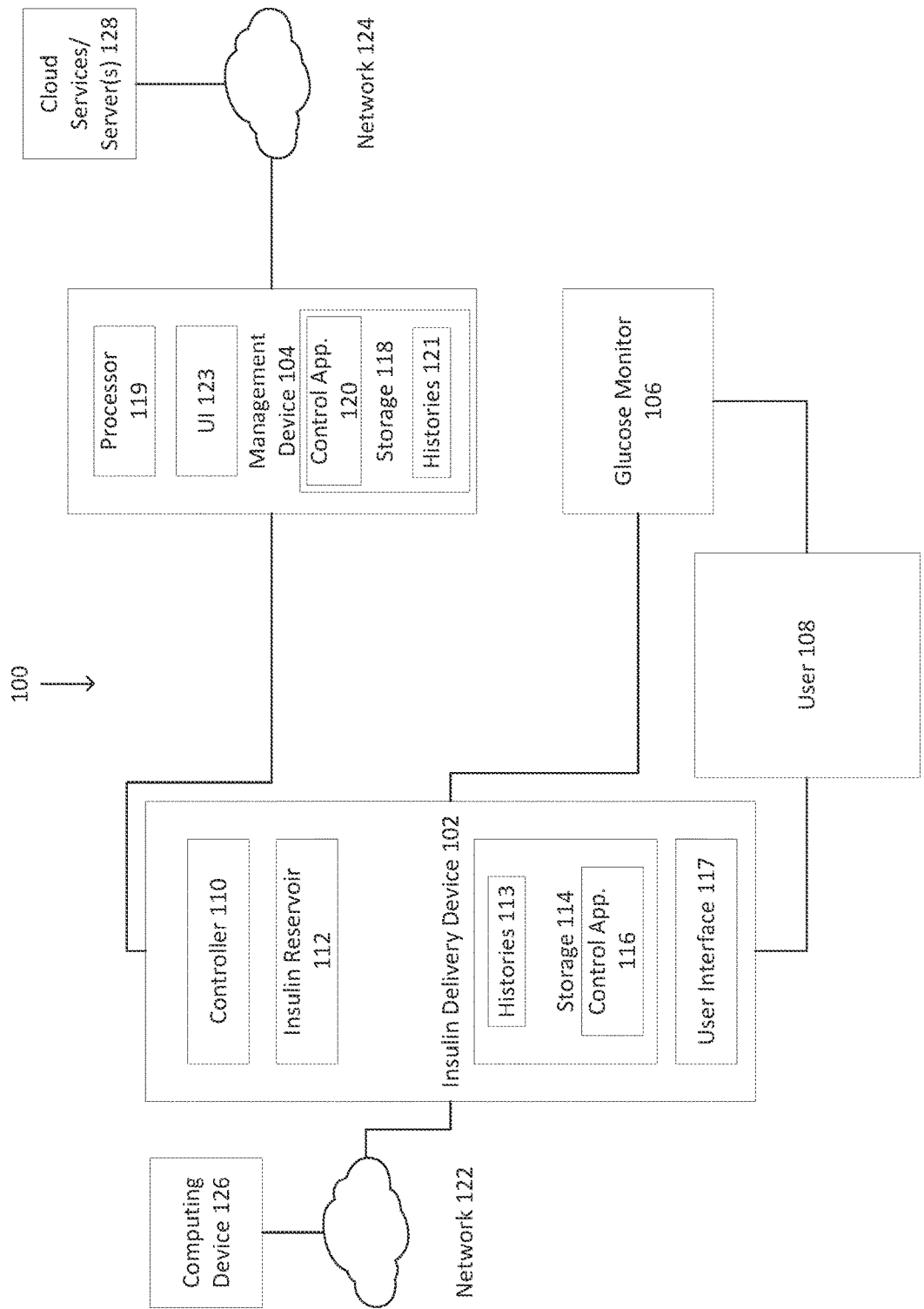
FIG. 1 depicts an environment including an AID system suitable for practicing an exemplary embodiment.

FIG. 1 depicts an illustrative drug delivery system (100) that is suitable for delivering insulin to a user (108) in an exemplary embodiment. The drug delivery system (100) includes an insulin delivery device (102). The insulin delivery device (102) may be a wearable device that is worn on the body of the user (108). The insulin delivery device (102) may be directly coupled to a user (e.g., directly attached to a body part and/or skin of the user (108) via an adhesive or the like). In an example, a surface of the insulin delivery device (102) may include an adhesive to facilitate attachment to the user (108).

The insulin delivery device (102) may include a controller (110). The controller (110) may be implemented in hardware, software, or any combination thereof. The controller (110) may, for example, be a microprocessor, a logic circuit, a field programmable gate array (FPGA), an application specific integrated circuit (ASIC) or a microcontroller coupled to a memory. The controller (110) may maintain a date and time as well as other functions (e.g., calculations or the like). The controller (110) may be operable to execute a control application (116) stored in the storage (114) that enables the controller (110) to direct operation of the insulin delivery device (102). The storage (114) may hold histories (113) for a user, such as a history of automated insulin deliveries, a history of bolus insulin deliveries, meal event history, exercise event history and the like. In addition, the controller (110) may be operable to receive data or information. The storage (114) may include both primary memory and secondary memory. The storage may include random access memory (RAM), read only memory (ROM), optical storage, magnetic storage, removable storage media, solid state storage or the like.

The insulin delivery device (102) may include an insulin reservoir (112) for storing insulin for delivery to the user (108) as warranted. A fluid path to the user (108) may be provided, and the insulin delivery device (102) may expel the insulin from the insulin reservoir (112) to deliver the insulin to the user (108) via the fluid path. The fluid path may, for example, include tubing coupling the drug delivery device (102) to the user (108) (e.g., tubing coupling a cannula to the insulin reservoir (112)).

There may be one or more communications links with one or more devices physically separated from the insulin delivery device (102) including, for example, a management device (104) of the user and/or a caregiver of the user and/or a glucose monitor (106). The communication links may include any wired or wireless communication link operating according to any known communications protocol or standard, such as Bluetooth®, Wi-Fi, a near-field communication standard, a cellular standard, or any other wireless protocol The insulin delivery device (102) may also include a user interface (117), such as an integrated display device for displaying information to the user (108) and in some embodiments, receiving information from the user (108). The user interface (117) may include a touchscreen and/or one or more input devices, such as buttons, knob or a keyboard.

The insulin delivery device (102) may interface with a network (122). The network (122) may include a local area network (LAN), a wide area network (WAN) or a combination therein. A computing device (126) may be interfaced with the network, and the computing device may communicate with the insulin delivery device (102).

The drug delivery system 100 may include a glucose monitor (106) for sensing the blood glucose concentration levels of the user (108). The glucose monitor (106) may provide periodic blood glucose concentration measurements and may be a continuous glucose monitor (CGM), or another type of device or sensor that provides blood glucose measurements. The glucose monitor (106) may be physically separate from the insulin delivery device (102) or may be an integrated component thereof. The glucose monitor (106) may provide the controller (110) with data indicative of measured or detected blood glucose levels of the user (108). The glucose monitor (106) may be coupled to the user (108) by, for example, adhesive or the like and may provide information or data on one or more medical conditions and/or physical attributes of the user (108). The information or data provided by the glucose monitor (106) may be used to adjust drug delivery operations of the insulin delivery device (102).

The drug delivery system (100) may also include the management device (104). The management device (104) may be a special purpose device, such as a dedicated personal diabetes manager (PDM) device. The management device (104) may be a programmed general purpose device, such as any portable electronic device including, for example, a dedicated controller, such as processor, a smartphone, or a tablet. The management device (104) may be used to program or adjust operation of the drug delivery device (102) and/or the sensor (104). The management device (104) may be any portable electronic device including, for example, a dedicated controller, a smartphone, or a tablet. In the depicted example, the management device (104) may include a processor (119) and a storage (118). The processor (119) may execute processes to manage a user's blood glucose levels and for control the delivery of the drug or therapeutic agent to the user (108). The processor (119) may also be operable to execute programming code stored in the storage (118). For example, the storage may be operable to store one or more control applications (120) for execution by the processor (119). The storage (118) may store the control application (120), histories (121) like those described above for the insulin delivery device (102) and other data and/or programs.

The management device (104) may include a user interface (123) for communicating with the user (108). The user interface may include a display, such as a touchscreen, for displaying information. The touchscreen may also be used to receive input when it is a touch screen. The user interface (123) may also include input elements, such as a keyboard, button, knobs or the like.

The management device 104 may interface with a network (124), such as a LAN or WAN or combination of such networks. The management device (104) may communicate over network (124) with one or more servers or cloud services (128). The role that the one or more servers or cloud services (128) may play in the exemplary embodiments will be described in more detail below.

Figure 2:
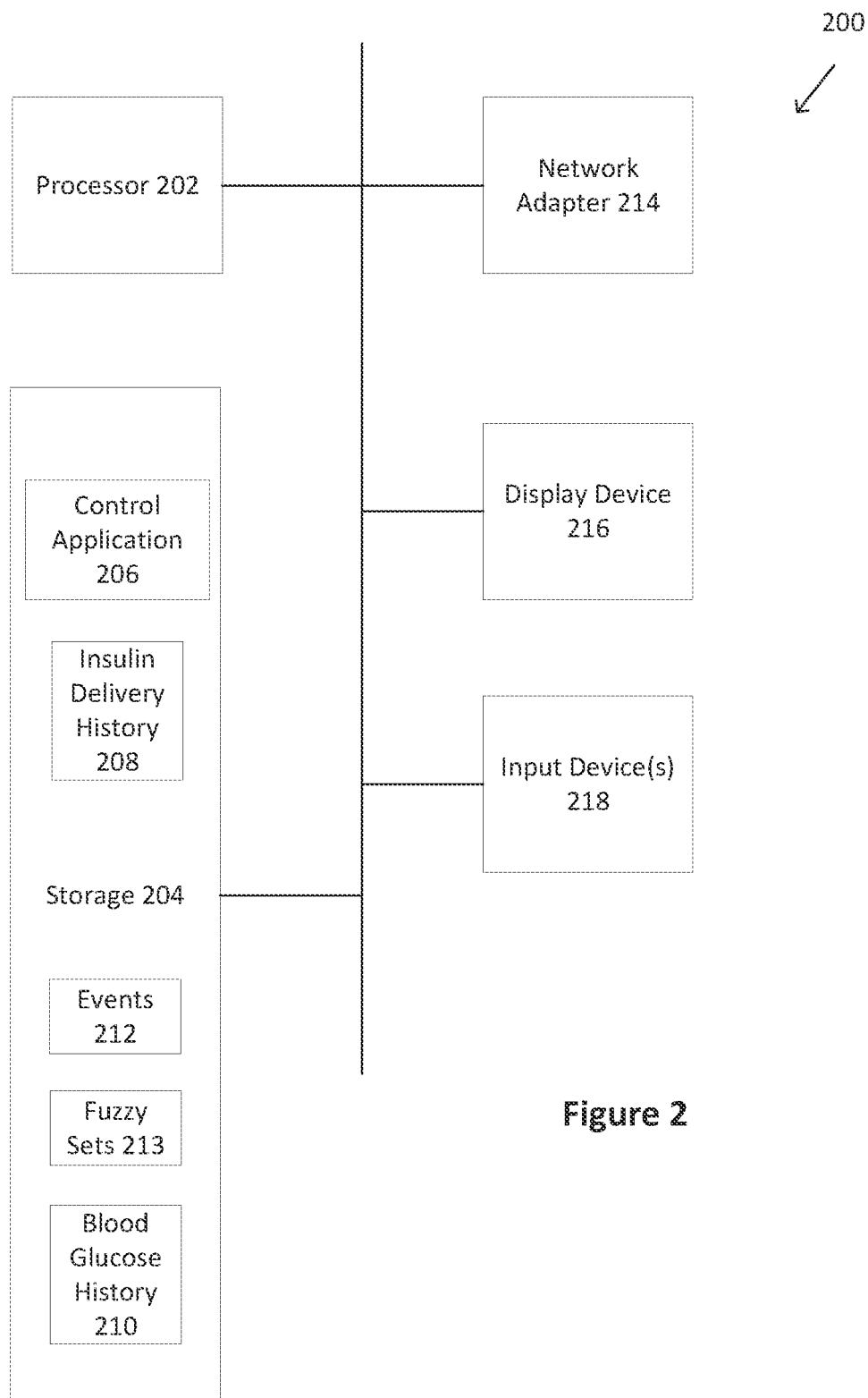
FIG. 2 depicts a block diagram of a device suitable for performing methods of exemplary embodiments described herein.

FIG. 2 depicts a block diagram of a device (200) suitable for performing the methods that will be described in more detail below. The device (200) may in different exemplary embodiments be the insulin delivery device (102), the management device (104), the computing device (126) or the one or more servers (128). Where the device is the computing device (126), or the one more servers or cloud services (128), the device (200) may act in cooperation with the management device (104) and the insulin delivery device (102) to perform the methods. The device (200) includes a processor (202) for executing programming instructions. The processor (202) has access to a storage (204). The storage (204) may store an application (206) for performing the methods. This application (206) may be executed by the processor (202). The storage (204) may store an insulin delivery history (208) for the user. The insulin delivery history (208) may contain data regarding the amount of insulin delivered as well as the date and time of the deliveries. The insulin delivery history (208) may also identify if each delivery is a basal delivery or a bolus delivery. The storage (204) may store the blood glucose history (210). The blood glucose history (210) may include blood glucose concentration readings as well as the date and time of such readings. These values may be obtained by the glucose monitor (106). The storage (204) additionally may store information regarding events (212), like meal events and exercise events. The storage may hold information regarding the fuzzy sets (213), including their associated member functions.

The device (200) may include a network adapter (214) for interfacing with networks, like networks (122 and 124). The device (200) may have a display device (216) for displaying video information. The display device (216) may be, for instance, a liquid crystal display (LCD) device, a light emitting diode (LED) device, etc. The device (200) may include one or more input devices (218) for enabling input to be received. Examples of input devices include keyboards, mice, pointing devices, touchscreen displays, button, knobs or the like.

Figure 3:
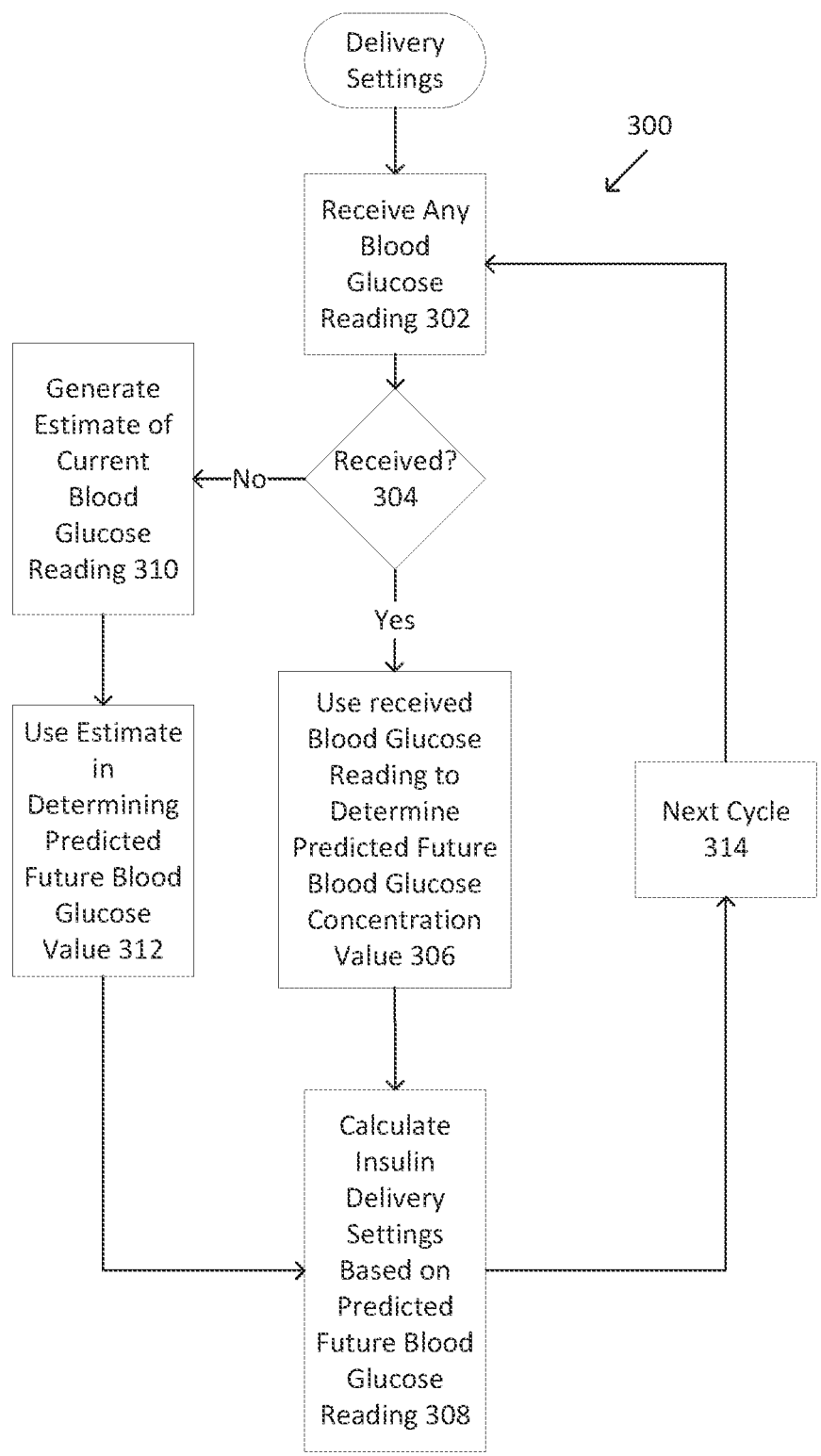
FIG. 3 depicts a flowchart showing illustrative steps for determining insulin delivery settings in an exemplary embodiment.

As was discussed above, the device (200) (such as the insulin delivery device (102)) may perform the steps depicted in the flowchart (300) to set insulin delivery settings for the user. For purposes of the discussion below it will be assumed that the device (200) is the insulin delivery device (102). The insulin delivery settings may include but are not limited to what dosage of insulin to deliver to a user and when to deliver the insulin to the user. The dosage amount may be zero in instances where it is determined that insulin delivery is to be suspended. As shown in FIG. 3, the device (200), such as insulin delivery device (102), receives any blood glucose concentration reading (302) sent from the glucose monitor (106). As was discussed above, there is a wireless connection between the glucose monitor (106) and the insulin delivery device (102) and that wireless connection is used to transmit blood glucose concentration readings from the glucose monitor (106) to the insulin delivery device (102). If the wireless connection fails or is compromised such that the blood glucose concentration reading may not reach the insulin delivery device (102), the exemplary embodiment takes steps to remediate the situation. If the insulin delivery device (102) receives the current blood glucose concentration reading (see 304), the current blood glucose concentration reading is used to determine a predicted future blood glucose concentration value for the user (306).

One suitable way for determining the predicted future blood glucose concentration value in (306) may be expressed by the following equation:

$$G_p(k+1) = b_0 G_{new}(k) + b_1 G_{new}(k-1) + \cdots b_n G_{new}(k-n) + I(k-1) + I(k-2) + \cdots I(k-n)$$

where $G_p(k+1)$ is the predicted future blood glucose concentration value at control cycle k, $G_{new}(k)$ is the blood glucose concentration reading for control cycle k, $b_i$ is a weighting coefficient for the ith control cycle before the current control cycle and I(k) is the insulin action for insulin delivered during the kth control cycle.

The predicted future blood glucose concentration value for the next control cycle is then used to set the insulin delivery settings in (308). The next cycle may the begin (314) and the process repeats with (302).

If at (304) it is determined that the blood glucose concentration reading has not been received, an estimate of the blood glucose concentration reading is determined (310). As was mentioned above, a number of different approaches may be used to generate this estimate. The discussion below details several options for generating the estimate. The estimate is used in determining the predicted future blood glucose concentration value in place of the missing reading (312).

Figure 4:
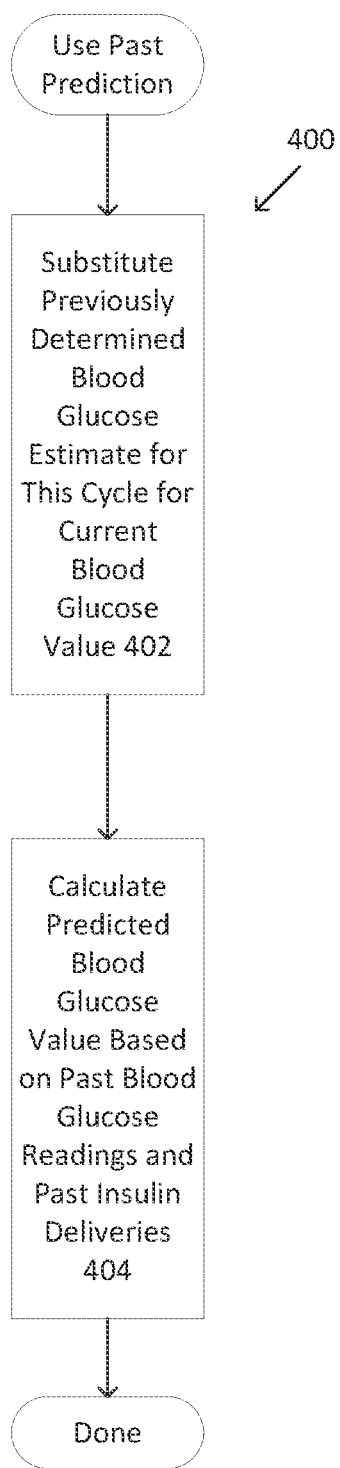
FIG. 4 depicts a flowchart showing illustrative steps for generating an estimate of a blood glucose concentration reading from a past prediction of the blood glucose concentration reading.

A first option for determining the estimate of the current blood glucose concentration reading is to rely on the previous prediction of the blood glucose concentration reading for the current control cycle. FIG. 4 depicts a flowchart (400) of steps that may be performed. The insulin delivery device (102) is an AID device and determines predicted blood glucose concentration readings as part of its control process. The insulin delivery device (102) has determined a predicted blood glucose concentration reading for the current control cycle. As such, a first option is to replace the missing blood glucose concentration reading with the predicted blood glucose concentration reading (402). The replacement value is used to predict the next predicted future blood glucose concentration reading (404). Modifying the equation set forth above to account for the replacement, the equation may be expressed as:

$$G(k+1) = b_0 G_p(k) + b_1 G_{new}(k-1) + \cdots b_n G_{new}(k-n) + I(k-1) + I(k-2) + \cdots I(k-n)$$

where $G_p(k)$ is the predicted future blood glucose concentration reading for control cycle k.

Figure 5:
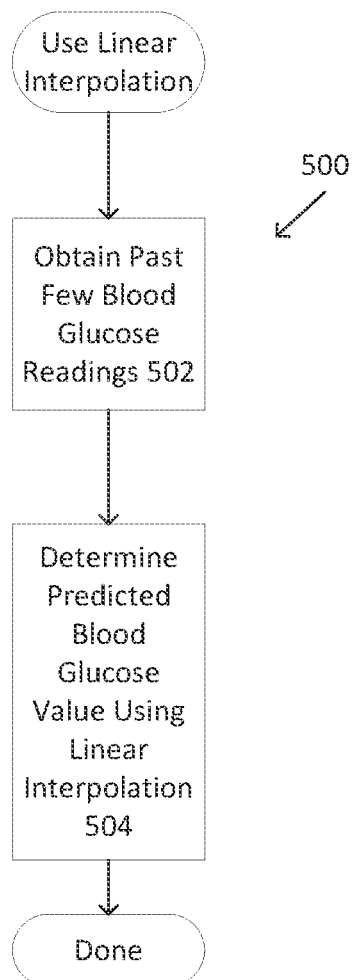
FIG. 5 depicts a flowchart showing illustrative steps for generating an estimate of a blood glucose concentration reading using interpolation.

Another option for determining the estimate of the current blood glucose concentration reading is to use linear interpolation. FIG. 5 depicts a flowchart (500) of illustrative steps for this approach. The notion behind this approach is to capture the trend in blood glucose concentration values and to generate an estimate based on that trend. The past few blood glucose concentration readings are obtained (502). This may be a suitable number of readings, such as, for example, two to four readings. The predicted future blood glucose concentration value is then determine using linear interpolation (504). For instance, linear interpolation may be used to identify the trend in blood glucose concentration readings and based on that trend, the predicted future blood glucose concentration value may be determined. Suppose that one chooses to obtain two blood glucose concentration values, in that case the predicted future blood glucose concentration value may be calculated as:

$$G_p(k+1) = G(k) + \frac{G(k) - G(k-2)}{2}$$

The value $$\frac{G(k) - G(k-2)}{2}$$

may be viewed as determining the average delta over two cycles between the blood glucose concentration readings and is added to the most recent blood glucose concentration reading to determine the predicted future blood glucose concentration value $G_p(k+1)$.

Figure 6:
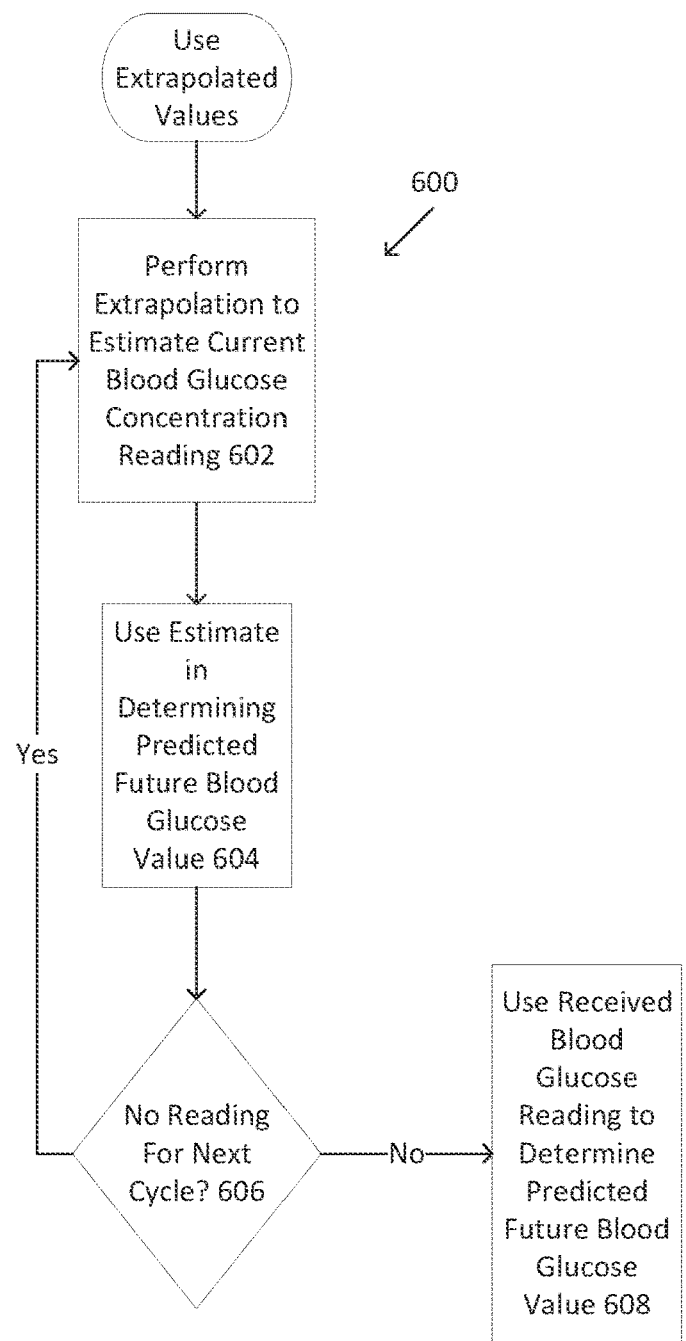
FIG. 6 depicts a flowchart showing illustrative steps for generating an estimate of a blood glucose concentration reading using extrapolation.

In some instances, multiple successive blood glucose concentration readings over consecutive control cycle may be missed due to issues with the wireless connection. In such an instance, extrapolated values may be used to generate successive estimates for the successive control cycle. FIG. 6 depicts a flowchart (600) of illustrative steps that may be performed to obtain such estimates. Extrapolation is performed to obtain an estimate of the blood glucose concentration reading for the control cycle (602). Linear extrapolation may be used by identifying a line that passes through the most recently received blood glucose concentration readings and finding the point on the line for the current control cycle to determine the estimate of the missing blood glucose concentration reading. The resulting estimate is used in predicting the predicted future blood glucose concentration value (604). If during the next control cycle the blood glucose concentration reading is missing (606), the process is repeated to generate an estimate for that control cycle using extrapolation beginning at (602). If there is a blood glucose concentration reading received, that received reading is used in predicting the predicted future blood glucose concentration value (608).

Figure 7:
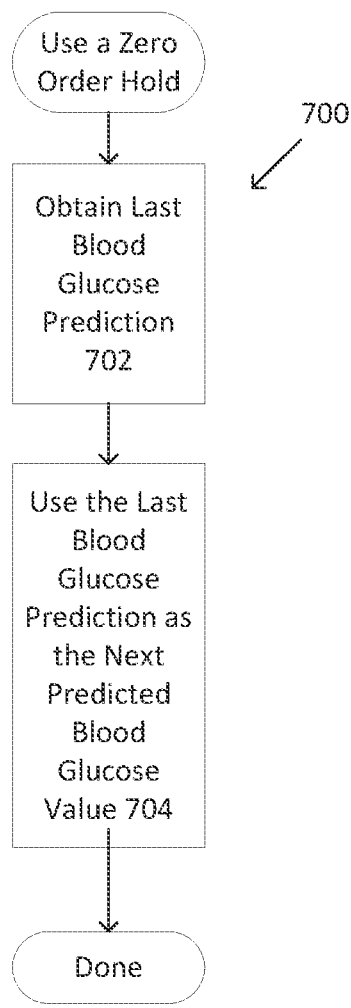
FIG. 7 depicts a flowchart showing illustrative steps for generating an estimate of a blood glucose concentration reading using a zero order hold.

One computationally inexpensive option is to use a zero order hold. As shown in flowchart 700 in FIG. 7 for that case, a most recent predicted blood glucose concentration value is obtained (702). The most recent previous blood glucose reading is maintained as the next predicted blood glucose concentration value (704).

Figure 8A:
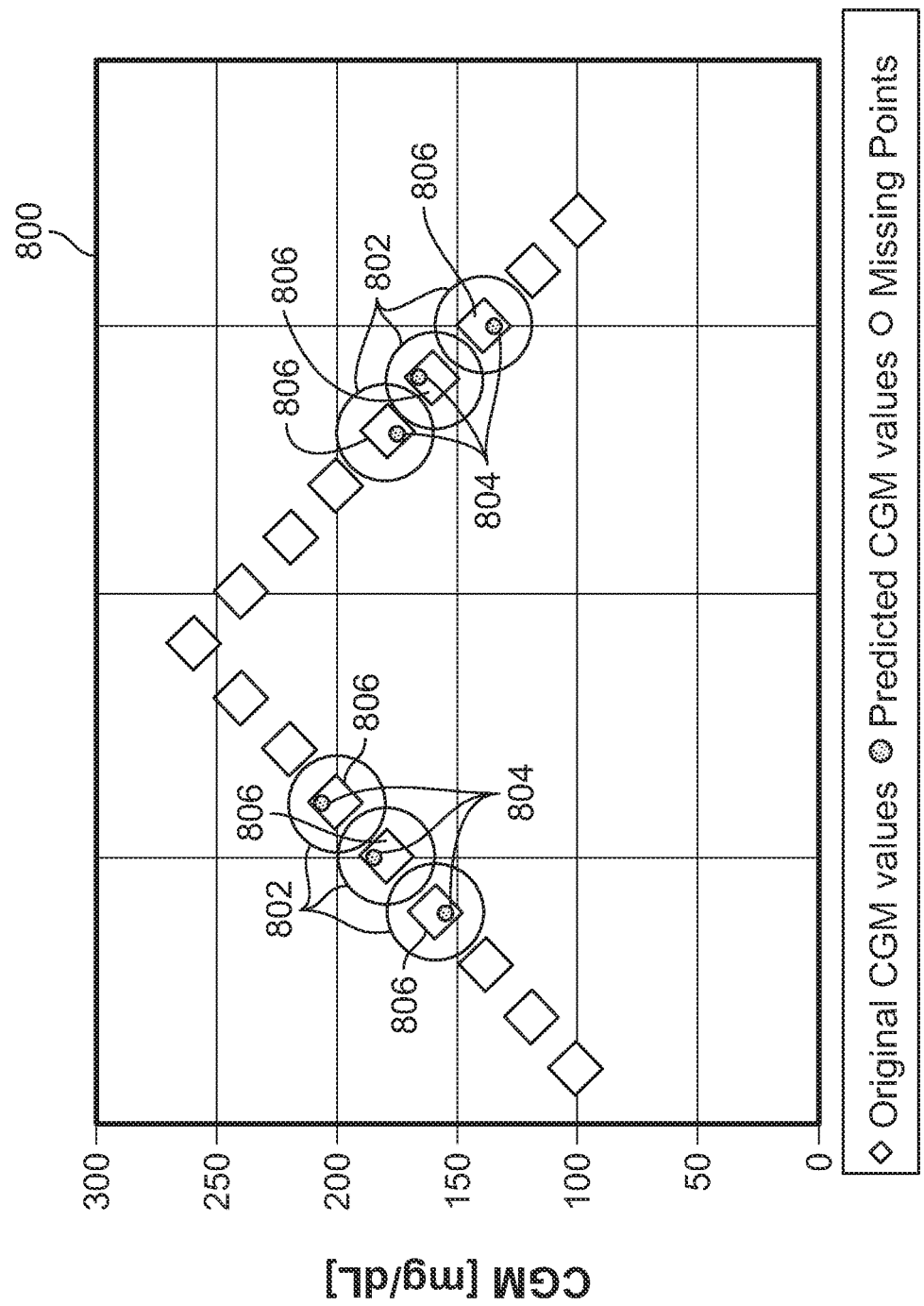
FIG. 8A shows an illustrative plot of blood glucose concentration values over time for a user.

The above described approaches to estimating missing blood glucose concentration readings may be quite effective. FIG. 8A shows an illustrative plot (800) of blood glucose concentration values over time for a user. The plot shows, missing values (802), the estimated values (804) and the actual blood glucose values that were missed and later backfilled. The plot (800) illustrated that the estimates act as accurate proxies of the missing blood glucose concentration values.

Figure 8B:
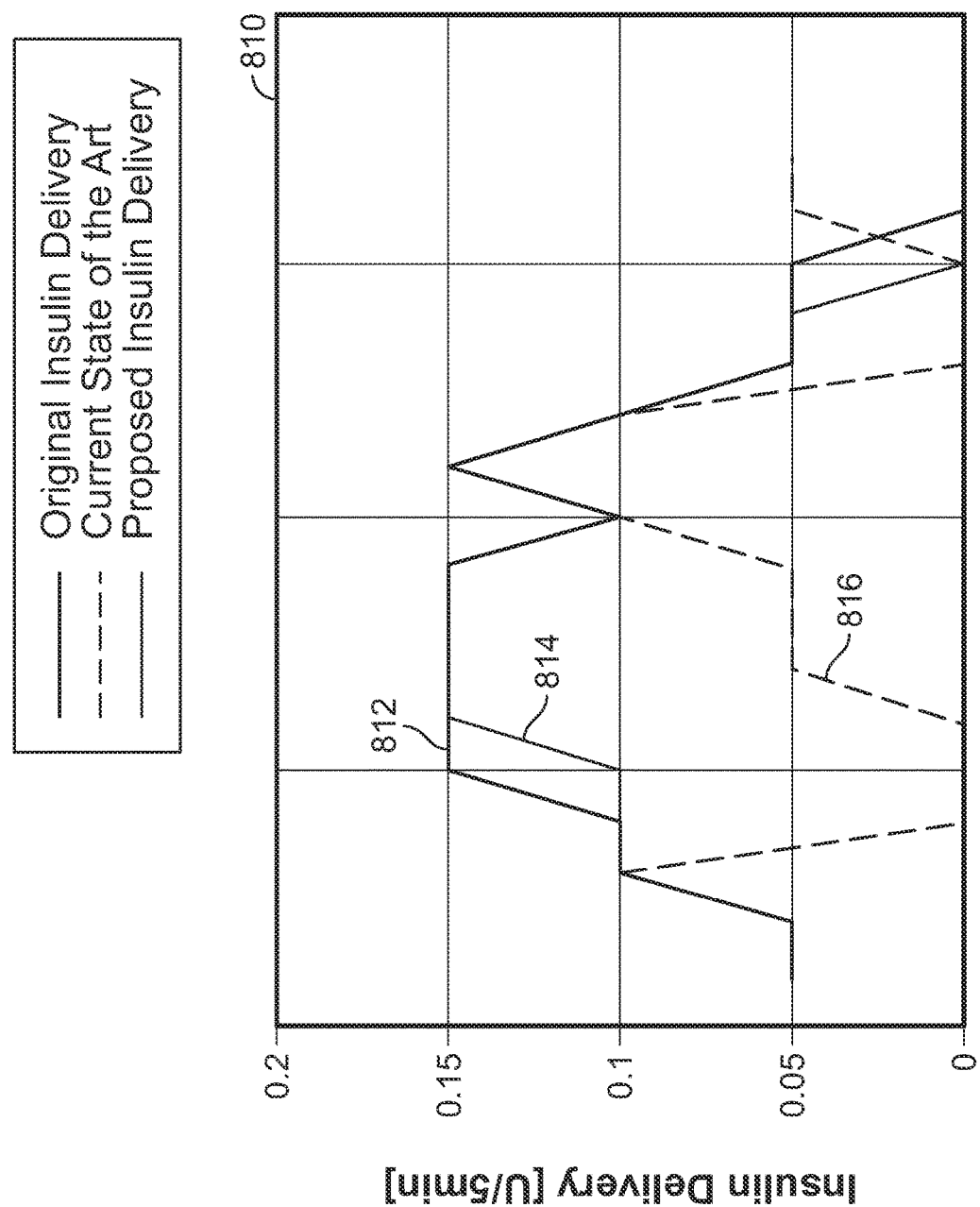
FIG. 8B depicts a plot of three curves of insulin delivery for different approaches for a user over time using an AID device.

FIG. 8B depicts a plot (810) of three curves of insulin delivery for a user over time using an AID device. Curve (812) captures the insulin delivery dosages by the AID over time for an instance where no blood glucose concentration readings are missed. Curve (814) captures the insulin delivery dosages over time for an exemplary embodiment where estimates are used for missing blood glucose concentration readings. As can be seen, curve (814) closely approximates curve (812). This is evidence that the exemplary embodiments may produce results that closely approximate the behavior of an AID system without missing blood glucose concentration readings. In contrast, curve (816) captures the insulin delivery dosages over time for a conventional AID system that suspends deliveries responsive to missing blood glucose concentration readings. Curve (816) diverges significantly from curve (812).

Figure 9:
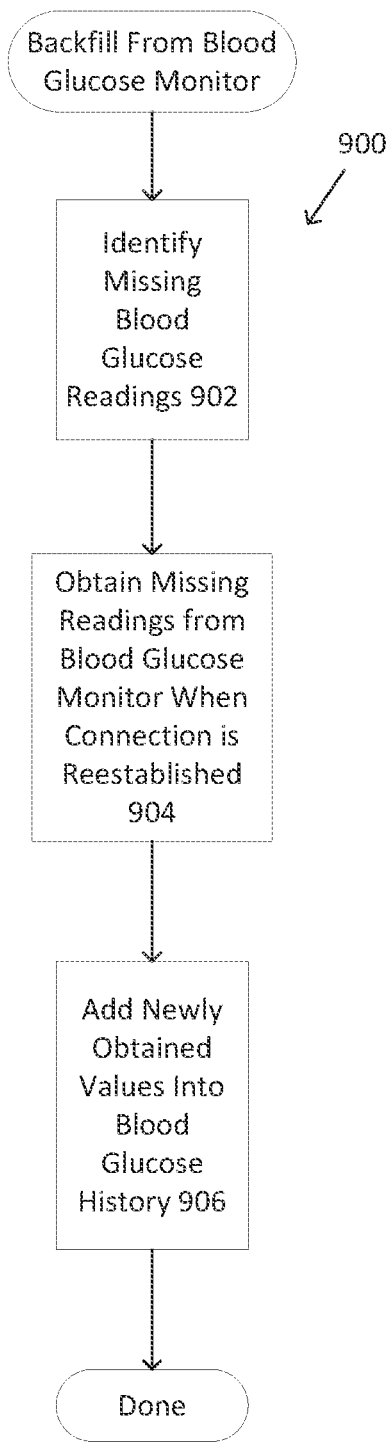
FIG. 9 depicts a flowchart showing illustrative steps for backfilling missing blood glucose concentration readings with later received blood glucose concentration readings form a glucose monitor.

Exemplary embodiments may provide the ability to backfill missing blood glucose concentration readings once a wireless connection between the glucose monitor (106) and insulin delivery device (102) is restored. FIG. 9 depicts a flowchart (900) of steps that may be performed to backfill missing blood glucose concentration readings. First, the insulin delivery device (102) must identify the missing blood glucose concentration readings (902). The insulin delivery device (102) may flag when a blood glucose concentration reading is not received and thus may be aware of what readings are missing. When the wireless connection is reestablished, the missing blood glucose concentration readings may be received (904) at the insulin delivery device (102) from the glucose monitor (106). The glucose monitor (106) may send the missing readings as a matter of course when the connection is reestablished, or the insulin delivery device (102) may request the missing readings. The missing blood glucose concentration readings are then added to the blood glucose concentration reading history (210) stored (906) at the insulin delivery device (102 and 200).

These values then may be used in generating predicted future blood glucose concentration values as discussed above. In the exemplary embodiments, the general system states utilized to calculate the new prediction trends of the system $x_0$, $x_1$, and $x_2$ can be determined using the backfill $CGM_b(t)$ available after re-establishment of system communication in the $n^{th}$ control cycle as:

$$\begin{bmatrix} x_0(n) \\ x_1(n) \\ x_2(n) \end{bmatrix} = \begin{bmatrix} CGM_b(n-2) - SP \\ CGM_b(n-1) - SP \\ CGM_b(n) - SP \end{bmatrix}$$

where SP is the user's target.

Figure 10:
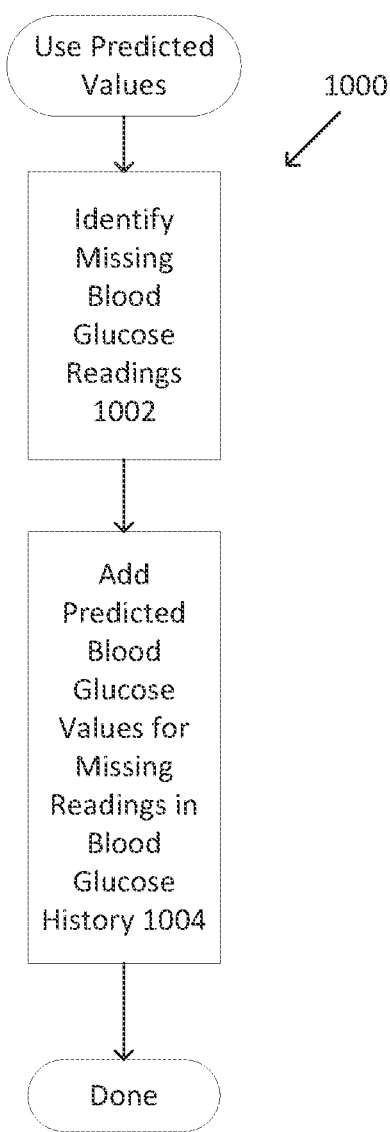
FIG. 10 depicts a flowchart showing illustrative steps for backfilling missing blood glucose concentration readings with predicted blood glucose concentration readings.

The backfilling need not be with past blood glucose concentration readings from the glucose monitor (106); rather the precited blood glucose concentration readings may be used instead. FIG. 10 depicts a flowchart (1000) of illustrative steps that may be performed in such an instance. Initially, the missing blood glucose concentration readings are identified (1002), such as was described above. Then the predicted blood glucose concentration readings for the corresponding control cycles are backfilled (1004) into the blood glucose concentration history (210) and may be used to predict future blood glucose concentration values.

While the present invention has been described herein relative to exemplary embodiments thereof, it will be appreciated that various changes in form and detail may be made without departing from the intended scope as defined in the appended claims.

The invention claimed is:

1. An electronic device, comprising:
    a wireless interface with a glucose sensor for providing glucose level readings of a user;
    a storage medium storing programming instructions; and
    a processor for executing the programming instructions in the storage medium to:
        where a current glucose level reading for the user is successfully received over the wireless interface from the glucose sensor for a current control cycle, set insulin delivery settings for delivery of the insulin to the user from an automated insulin delivery (AID) device for the current control cycle based on predicted future glucose level readings for the user, wherein the predicted future glucose level readings are based on, at least in part, glucose level readings from the glucose sensor from previous control cycles; and
        where the current glucose level reading for the user is not successfully received over the wireless interface from the glucose sensor for the current control cycle, estimate the glucose level reading that was not successfully received over the wireless interface from the glucose sensor, and set the insulin delivery settings for delivery of the insulin to the user from the AID device for the current control cycle based on the predicted future glucose level readings for the user, wherein the predicted future glucose level readings are based on the glucose level readings from the glucose sensor from previous control cycles and the estimate of the current glucose level reading that was not successfully received over the wireless interface from the glucose sensor.

2. The electronic device of claim 1, wherein the estimate of the current glucose level reading is one of the predicted future glucose level readings.

3. The electronic device of claim 1, wherein the estimate of the current glucose level reading is determined by applying interpolation of glucose level readings from the glucose sensor from previous control cycles.

4. The electronic device of claim 3, wherein the estimate of the of the current glucose level reading is determined by summing a most recent received glucose level reading with an average change between most recent ones of the glucose level readings.

5. The electronic device of claim 1, wherein the estimate of the current glucose level reading is a most recently received glucose level reading.

6. A method performed by a processor, comprising:
    where a current glucose level reading for a user is successfully received by an automated insulin delivery (AID) device over a wireless interface from the glucose sensor for a current control cycle, setting insulin delivery settings for delivery of the insulin by the AID device to the user of the AID device for the current control cycle based on predicted future glucose levels for the user, wherein the predicted future glucose levels are based, at least in part, on glucose level readings from the glucose sensor for previous control cycles; and where the glucose level reading for the user is not successfully received by the AID device over the wireless interface from the glucose sensor for the current control cycle, estimating the current glucose level reading that was not successfully received over the wireless interface from the glucose sensor, and setting the insulin delivery settings for delivery of the insulin to the user for the current control cycle based on the predicted future glucose levels for the user, wherein the predicted future glucose levels are based on the glucose level readings from the glucose sensor from previous control cycles and the estimate of the current glucose level reading that was not successfully received over the wireless interface from the glucose sensor.

7. The method of claim 6, wherein the estimate of the current glucose level reading is one of the predicted future glucose levels.

8. The method of claim 6, wherein the estimate of the current glucose level reading is determined by applying interpolation of glucose level readings from the glucose sensor for previous control cycles.

9. The method of claim 8, wherein the estimate of the of the current glucose level reading is determined by summing a most recently received glucose level reading with an average change between most recent ones of the glucose level readings received from the glucose sensor.

10. The method of claim 9, wherein the estimate of the of the current glucose level reading is determined by summing a most recently received glucose level reading with an average change between two most recent ones of the glucose level readings received from the glucose sensor.

11. The method of claim 6, wherein the estimate of the current blood glucose level reading is a most recently received glucose level reading.

12. A method performed by an automated insulin delivery (AID) device, comprising:
receiving glucose level readings for a user from a glucose sensor over a wireless interface at the AID device for control cycles;
where, for a given control cycle, a glucose level reading for the user is not received at the AID device from the glucose sensor over the wireless interface, determining an estimate of the glucose level reading for the user for the given control cycle;
using the received blood glucose level readings and the determined estimate for the given control cycle to predict a future glucose level reading;
setting insulin delivery settings of the AID device based on the predicted future glucose level for the user; and
when communication over the wireless interface with the glucose sensor is reestablished, replacing the estimate of the glucose level reading for the user for the given control cycle with a glucose level reading for the user from the glucose monitor for the given cycle in determining an estimate of the glucose level reading for the user for a next control cycle.

13. The method of claim 12, wherein the determining the estimate of the glucose level reading for the user for the given control cycle comprises determining a trend of glucose level values from the received glucose level readings and using the trend to determine the estimate.

14. The method of claim 13, wherein the using the trend of glucose level values comprises performing extrapolation based on the trend to obtain the estimate or performing interpolation based on the trend to obtain the estimate.

15. The method of claim 12, further comprising using the using the glucose level reading for the given cycle in setting the insulin delivery settings of the AID device.

16. A non-transitory computer-readable storage medium storing instructions that when executed by a processor cause the processor to:
receive glucose level readings for a user from a glucose sensor over a wireless interface at the AID device for control cycles, wherein during normal operation a glucose level reading is received for each of the control cycles;
where, for a given control cycle, a glucose level reading for the user is not received at the AID device from the glucose sensor over the wireless interface, determine an estimate of the glucose level reading for the user for the given control cycle;
use the received glucose level readings and the determined estimate for the given control cycle to predict a future glucose level reading;
set insulin delivery settings of the AID device based on the predicted future glucose level for the user; and
when communication over the wireless interface with the glucose sensor is reestablished, replace the estimate of the glucose level reading for the user for the given control cycle with a glucose level reading for the user from the glucose monitor for the given cycle in determining an estimate of the glucose level reading for the user for a next control cycle.

17. The non-transitory computer-readable storage medium of claim 16, wherein the determining an estimate of the glucose level reading for the user for the given control cycle comprises determining a trend of glucose level values from the received glucose level readings and using the trend to determine the estimate.

18. The non-transitory computer-readable storage medium of claim 16, wherein the using the trend comprises performing extrapolation based on the trend to obtain the estimate or performing interpolation based on the trend to obtain the estimate.

19. A non-transitory computer-readable storage medium storing instructions that when executed by a processor cause the processor to:
where a current glucose level reading for a user is successfully received by an automated insulin delivery (AID) device over a wireless interface from the glucose sensor for a current control cycle, set insulin delivery settings for delivery of the insulin by the AID device to the user for the current control cycle based on predicted future glucose levels for the user, wherein the predicted future glucose levels are based, at least in part, on glucose level readings from the glucose sensor for previous control cycles; and
where the glucose level reading for the user is not successfully received by the AID device over the wireless interface from the glucose sensor for the current control cycle, estimate the current glucose level reading that was not successfully received over the wireless interface from the glucose sensor, and set the insulin delivery settings for delivery of the insulin to the user for the current control cycle based on the predicted future glucose levels for the user, wherein the predicted future glucose levels are based on the glucose level readings from the glucose sensor from previous control cycles and an estimate of the current glucose level reading that was not successfully received over the wireless interface from the glucose sensor.

20. The non-transitory computer-readable storage medium of claim 19, wherein the estimate of the current glucose level reading is one of the predicted future glucose levels for the current control cycle or determined by applying interpolation of blood glucose level readings from the glucose sensor from previous control cycles.

* * * * *

UNITED STATES PATENT AND TRADEMARK OFFICE
CERTIFICATE OF CORRECTION

PATENT NO. : 12,226,612 B2  
APPLICATION NO. : 17/715589  
DATED : February 18, 2025  
INVENTOR(S) : Yibin Zheng et al.

Page 1 of 1

It is certified that error appears in the above-identified patent and that said Letters Patent is hereby corrected as shown below:

In the Claims

Column 10, Claim 4, Line 54, delete "of the."

Column 11, Claim 9, Line 28, delete "of the."

Column 11, Claim 10, Line 33, delete "of the."

Signed and Sealed this  
Fourth Day of November, 2025

John A. Squires  
*Director of the United States Patent and Trademark Office*